(12) United States Patent
Nagasawa et al.

(10) Patent No.: US 7,436,562 B2
(45) Date of Patent: Oct. 14, 2008

(54) SCANNING EXAMINATION APPARATUS, LENS UNIT, AND OBJECTIVE-LENS ADAPTOR

(75) Inventors: Nobuyuki Nagasawa, Hino (JP); Yoshihisa Tanikawa, Tokyo (JP); Kazuhiko Osa, Hachioji (JP); Yoshiharu Saito, Hachioji (JP)

(73) Assignee: Olympus Corporation, Tokyo (JP)

( * ) Notice: Subject to any disclaimer, the term of this patent is extended or adjusted under 35 U.S.C. 154(b) by 267 days.

(21) Appl. No.: 11/375,042

(22) Filed: Mar. 15, 2006

(65) Prior Publication Data

US 2006/0214095 A1 Sep. 28, 2006

(30) Foreign Application Priority Data

Mar. 23, 2005 (JP) ............................. 2005-084262
Mar. 23, 2005 (JP) ............................. 2005-084263

(51) Int. Cl.
*G02B 26/08* (2006.01)
*G02B 21/06* (2006.01)

(52) U.S. Cl. ........................ 359/196; 359/205; 359/385; 359/388

(58) Field of Classification Search ........................ None
See application file for complete search history.

(56) References Cited

U.S. PATENT DOCUMENTS

| 5,903,688 | A | 5/1999 | Engelhardt et al. |
| 6,094,300 | A | 7/2000 | Kashima et al. |
| 6,388,807 | B1 | 5/2002 | Knebel et al. |
| 6,437,913 | B1 | 8/2002 | Kishi |
| 2001/0042837 | A1 | 11/2001 | Hoffmann |

(Continued)

FOREIGN PATENT DOCUMENTS

DE 10039520 2/2002

(Continued)

OTHER PUBLICATIONS

European Office Action dated Nov. 9, 2007 for corresponding EP Application No. 06 005 109.1—1524, 6 pp.

*Primary Examiner*—James Phan
(74) *Attorney, Agent, or Firm*—Pillsbury Winthrop Shaw Pittman LLP

(57) ABSTRACT

It is possible to easily and accurately confirm the position of an optical axis of an objective lens relative to an examination site on a specimen, and positioning of the objective relative to the specimen can be carried out rapidly in a preparation stage. The invention provides scanning examination apparatus comprising a first light source; a light scanning unit configured to scan light from the first light source on a specimen; an objective lens configured to form an image of the light scanned in the light scanning unit at the specimen; a light-detecting unit configured to detect return light emitted from the specimen; a second light source configured to emit visible light; a deflecting optical element, disposed between the light scanning unit and the objective lens, for making visible light emitted from the second light source enter the objective lens along an optical axis of the objective lens; and a beam-shaping unit configured to form the visible light from the second light source, which is irradiated onto a surface of the specimen via the objective lens using the deflecting optical element, into a pattern that enables the optical axis of the objective lens to be indicated.

16 Claims, 12 Drawing Sheets

U.S. PATENT DOCUMENTS

| | | |
|---|---|---|
| 2002/0163717 A1 | 11/2002 | Lee |
| 2005/0063051 A1 | 3/2005 | Lange et al. |
| 2006/0103921 A1* | 5/2006 | Karaki ....................... 359/368 |

FOREIGN PATENT DOCUMENTS

| | | |
|---|---|---|
| DE | 103 32 074 A1 | 2/2005 |
| JP | 4-294253 | 10/1992 |
| JP | 2000-275529 | 10/2000 |
| JP | 2001194123 | 7/2001 |
| JP | 2004093982 | 3/2004 |
| JP | 2005-031425 | 2/2005 |
| WO | 2005096058 A1 | 10/2005 |

* cited by examiner

SCANNING EXAMINATION APPARATUS, LENS UNIT, AND OBJECTIVE-LENS ADAPTOR

BACKGROUND OF THE INVENTION

1. Field of the Invention

The present invention relates to a scanning examination apparatus, lens unit, and objective-lens adaptor. This application is based on Japanese Patent Applications Nos. 2005-084262 and 2005-084263, the contents of which are incorporated herein by reference.

2. Description of Related Art

Known scanning examination apparatuses in the related art include, for example, scanning laser microscopes (for example, see Japanese Unexamined Patent Application Publication No. 2000-275529).

A scanning laser microscope two-dimensionally scans a specimen by imaging laser light emitted from a laser light source onto the specimen using an objective lens, via proximity galvanometer mirrors. By scanning the specimen with laser light in this way, the scanning laser microscope splits off fluorescence generated in the specimen and returning via the objective lens and the proximity galvanometer mirrors from the incident laser light and detects it.

Therefore, in such a scanning examination apparatus, there is a problem in that it is difficult to align the position of the optical axis of the objective lens and the site to be examined on the specimen.

More specifically, when examining the specimen using the scanning examination apparatus, in a preparation stage carried out before actual examination, the position of the objective lens is roughly aligned with the site to be examined on the specimen, and the objective lens is disposed opposite the specimen with a large gap provided therebetween as a working distance. However, in this preparation stage, where no light is emitted, the operator must instinctively perform alignment considering the shape of the specimen and the shape of the objective lens.

Furthermore, because the light radiated from the light source is two-dimensionally scanned on the specimen by the proximity galvanometer mirrors, even though light is emitted in the preparation stage, it is difficult to determine the optical axis position of the objective lens from the light spot, which is continually moving. It is particularly difficult to determine the position of the optical axis of the objective lens when the light from the light source is laser light. For example, when the wavelength of the laser light is not in the visible region, it is not possible to confirm the radiated region, similar to the above. Moreover, even if the wavelength of the laser light is in the visible region, it is difficult to perform alignment due to the dazzle effect peculiar to laser light. In addition, an operator should not directly observe the laser light irradiating the specimen.

In the related art, microscopes are used to perform magnified observation of specimens, such as biological specimens. A microscope objective lens unit attached to a microscope includes an infinity optical lens group formed of a plurality of lenses contained in a lens barrel that can be attached to and removed from the main body of the microscope (examination apparatus). With this microscope objective lens unit, a lens or flat plate at the extreme tip thereof is brought close to or in contact with the specimen to enable magnified observation of the specimen, which is disposed at the focal position (for example, see Japanese Unexamined Patent Application Publication No. 2005-031425).

However, in a standard microscope objective lens unit, the outer diameter of the lens barrel containing the lenses is large and is therefore not suitable for in-vivo examination of the conditions below the surface of a biological specimen, such as inside a laboratory animal or the like. Therefore, to observe the conditions below the surface of a biological specimen, it is first necessary to make an incision in the skin and muscular tissue of the laboratory animal, and then to make an incision in the surface of the target biological specimen, such as various internal organs, and to bring the end surface of the microscope objective lens unit into contact therewith. However, because the size of the microscope objective lens unit is large compared to a small laboratory animal, in order to observe the conditions below the surface of a biological specimen, it is necessary to make a large incision or a large hole in the specimen.

In such a case, since the region to be examined is directly behind the incision or hole in the surface of the specimen, the specimen may be significantly damaged by forming such an incision or hole, and therefore it is difficult to perform time-lapse observation over a long period of time. Since this method involves sewing up the region where the incision or hole is formed after examination and making another incision the next time examination is carried out, the biological specimen is inevitably damaged. Therefore, this method suffers from the disadvantage that it is difficult to examine the specimen under normal conditions over an extended period of time.

BRIEF SUMMARY OF THE INVENTION

The present invention has been conceived in light of the circumstances described above, and an object thereof if to provide a scanning examination apparatus that is capable of quickly and easily confirming the optical axis position of an objective lens with respect to a site to be examined on a specimen, and that can rapidly perform positioning of the objective lens with respect to the specimen during a preparation stage and can quickly obtain a desired image during an observation stage.

Furthermore, it is another object of the present invention to provide a lens unit and an objective-lens adaptor that enable simple and comparatively long-term in-vivo examination of biological tissue, such as cells and muscle tissue, or the conditions below the surface of various internal organs, such as the heart, liver, or brain, of mammals such as small laboratory animals and the like.

In order to realize the above-described object, the present invention provides the following solutions.

The present invention provides, in a first aspect, a scanning examination apparatus comprising a first light source; a light scanning unit configured to scan light from the first light source on a specimen; an objective lens configured to form an image of the light scanned in the light scanning unit at the specimen; a light-detecting unit configured to detect return light emitted from the specimen; a second light source configured to emit visible light; a deflecting optical element, disposed between the light scanning unit and the objective lens, for making visible light emitted from the second light source enter the objective lens along an optical axis of the objective lens; and a beam-shaping unit configured to form the visible light from the second light source, which is irradiated onto a surface of the specimen via the objective lens using the deflecting optical element, into a pattern that enables the optical axis of the objective lens to be indicated.

According to the present invention, the light emitted from the first light source is scanned by the light scanning unit and is irradiated onto the specimen via the objective lens. Therefore, by sequentially radiating the light from the first light source over a predetermined region on the specimen and detecting with the light-detecting unit return light returning from that irradiated region, via the objective lens and the light-scanning unit, it is possible to acquire a two-dimensional image of the specimen.

In such a case, in a preparation stage before examination is carried out, when the first light source is turned off and the second light source is operated, visible light emitted from the second light source is made incident on the objective lens by the deflecting optical element and irradiates the specimen. Because the visible light from the second light source forms a pattern that can indicate the optical axis position of the objective lens unit, using the beam-shaping unit, the operator can easily determine the position of the optical axis of the objective lens by looking at the visible light pattern irradiated on the surface of the specimen.

Then, by changing the position of the specimen relative to the objective lens in a direction intersecting the optical axis of the objective lens to align the visible light pattern on the specimen surface with the examination site on the specimen, it is possible to correctly position the optical axis of the objective lens. Also, by adjusting the distance between the objective lens and the specimen to adjust the focus of the visible light pattern on the surface of the specimen, it is possible to position the objective lens at the proper working distance from the specimen.

Then, after completing the preparation stage in this way, the second light source is turned off, the first light source is operated, the deflecting optical element is removed from between the light scanning unit and the objective lens, or light is made to pass through the deflecting optical system, and the light from the first light source is radiated onto the specimen through the objective lens. As a result, it is possible to rapidly examine the examination site on the specimen.

In the first aspect of the invention described above, the deflecting optical element is preferably formed of a mirror and is disposed so as to be insertable in and removable from between the light scanning unit and the objective lens.

By doing so, during the preparation stage where visible light from the second light source is incident on the specimen, the deflecting optical element, which is formed of a mirror, is inserted between the light scanning unit and the objective lens and stationary light, that is, light which is not scanned, from the second light source is irradiated onto the specimen, thus facilitating positioning of the objective lens. Furthermore, during the examination stage where light from the first light source is incident on the specimen, by removing the deflecting optical element from between the light scanning unit and the objective lens, scanned light from the first light source is incident on the specimen, and it is thus possible to detect the return light returning from the specimen with the light-detecting unit without causing any loss at the deflecting optical element.

In the first aspect of the invention described above, the deflecting optical element may be formed of a half-mirror. With this configuration, light from the first light source and light from the second light source can be made incident on the specimen while keeping the deflecting optical element inserted between the scanning unit and the objective lens. In such a case, during the preparation stage where light from the second light source is to be made incident on the specimen, turning off the first light source and operating the second light source enables detection of an image of the light from the second light source, the image being formed on the specimen surface, at the light detecting unit. As a result, it is possible to adjust the scanning region of the light scanning unit while observing, for example, an image constructed based on a detection signal from the light detecting unit.

In the first aspect of the invention described above, the beam-shaping unit may be capable of selectively switching the pattern of visible light from the second light source. With this configuration, it is possible to selectively switch between patterns according to the shape of the specimen surface and to radiate visible light. Therefore, positioning of the objective lens and the specimen is simplified, and it is thus possible to begin examination more quickly.

In the first aspect of the invention described above, the second light source may be a wavelength-switchable light source.

With this configuration, it is possible to radiate visible light having a wavelength that is appropriate for the color of the specimen surface. If the surface color differs from specimen to specimen, the images of the second light source on the sample surface would appear differently under visible light of the same wavelength. Therefore, by radiating visible light with a wavelength that allows the image of the light source to be discerned, according to the color of the specimen surface, the positioning of the objective lens and the specimen is simplified, and it is thus possible to start examination more quickly.

According to the present invention, by radiating the surface of the specimen with a stationary beam of visible light from the second light source, that is, without passing via the light scanning unit, it is possible to easily and accurately position the examination site of the specimen and the optical axis of the objective lens with the aid of the image of the second light source formed on the specimen. As a result, an advantage is afforded in that the time required for preparation prior to carrying out examination can be reduced, and overall, a desired examination image can be acquired more rapidly.

According to a second aspect, the first aspect of the invention described above may further comprise an examination apparatus main body; a lens unit configured to be removably attached to the examination apparatus main body, the lens unit including the objective lens; and a pointed insertion member formed of an optically transparent material, provided at the end of the lens unit to protrude along the optical axis, wherein the focal position of the lens unit is disposed outside the tip of the insertion member.

In this case, by attaching the lens unit to the examination apparatus main body, the pointed insertion member is positioned so as to protrude along the optical axis. Then, by bringing the lens unit close to the specimen and puncturing the specimen with the tip of the insertion member, it is possible to position the tip of the insertion member below the surface of the specimen. Because the focal position of the lens unit is located outside the tip of the insertion member, by carrying out examination in this state, illumination light or excitation light is imaged at a position below the specimen surface, and reflected light or fluorescence from the focal position can be observed. In this case, because the insertion member that punctures the specimen has a pointed shape, it is possible to observe the conditions below the specimen surface with minimal invasiveness.

A transmissive surface orthogonal to the optical axis may be provided at the tip of the insertion member. With this configuration, illumination light or excitation light guided through the lens unit from the examination apparatus main body is transmitted through the transmissive surface disposed at the tip of the insertion member, is emitted outside the lens unit, and is imaged at a focal position outside the tip of the insertion member. Then, by detecting reflected light or fluorescence returning from the focal position, it is possible to observe the conditions below the surface of a specimen disposed towards the front in the optical axis direction.

Furthermore, a reflecting mirror inclined relative to the optical axis may be provided at the tip of the insertion member.

With this configuration, illumination light or excitation light guided through the lens unit from the examination apparatus main body is reflected at the reflecting surface provided at the tip of the insertion member and is then imaged outside the tip of the insertion member. Because the reflecting surface is inclined with respect to the optical axis, it is possible to observe in the lateral direction with respect to the optical axis, which extends from the examination apparatus main body to the lens unit.

Furthermore, the first aspect of the invention described above may further comprise an examination apparatus main body; a lens unit including the objective lens; and an objective-lens adaptor attached to the end of the lens unit. The objective-lens adaptor may include a pointed insertion member formed of an optically transparent material and a mounting portion configured to attach the insertion member to the end of the lens unit in an on-axis manner, and when attached to the lens unit, the focal position of the lens unit is disposed outside the insertion member.

In this case, by attaching the mounting portion of the objective-lens adaptor to the end of the lens unit, the pointed insertion member is provided on the lens unit so as to protrude along the optical axis. Accordingly, it is possible to observe the conditions below the specimen surface with minimum invasiveness using a standard lens unit.

Furthermore, this objective-lens adaptor may include, at the tip of the insertion member, a transmissive surface orthogonal to the optical axis when the objective-lens adaptor is attached to the end of the lens unit.

Furthermore, this objective-lens adaptor may include, at the tip of the insertion member, a reflecting surface inclined relative to the optical axis when the objective-lens adaptor is attached to the end of the lens unit.

According to the present invention, an advantage is afforded in that it is possible to observe the conditions below the specimen surface with minimum invasiveness.

Therefore, it is possible to continue in-vivo observation of the specimen, such as a biological specimen, over a comparatively long period of time.

When the principal aim is to minimize the invasiveness to the specimen, it is possible to adopt the structures described in the following additional items.

Additional Item 1

A microscope objective lens unit configured to be attached to a microscope main body in a removable manner, wherein a pointed insertion member formed of an optically transparent material is provided at the end thereof so as to protrude along the optical axis, and a focal position is disposed outside a tip of the insertion member.

Additional Item 2

A microscope objective lens unit according to Additional Item 1, wherein a transmissive surface orthogonal to the optical axis is provided at the tip of the insertion member.

Additional Item 3

A microscope objective lens unit according to Additional Item 1, wherein a reflecting surface tilted with respect to the optical axis is provided at the tip of the insertion member.

Additional Item 4

An objective-lens adaptor configured to be attached to an end of a microscope objective lens unit, comprising a pointed insertion member formed of an optically transparent material and a mounting section configured to attach the insertion member to the end of the objective lens unit in an on-axis manner, wherein, when attached to the objective lens unit, the focal position of the objective lens unit is located outside the insertion member.

Additional Item 5

An objective-lens adaptor according to Additional Item 4, wherein a transmissive surface that is orthogonal to the optical axis when the objective-lens adaptor is attached to the end of the microscope objective lens unit is provided at the tip of the insertion member.

Additional Item 6

An objective-lens adaptor according to Additional Item 4, wherein a reflecting surface that is tilted with respect to the optical axis when the objective-lens adaptor is attached to the end of the microscope objective lens unit is provided at the tip of the insertion member.

DETAILED DESCRIPTION OF THE INVENTION

A scanning examination apparatus 1 according to a first embodiment of the present invention will be described below with reference to FIGS. 1 to 3.

Figure 1:
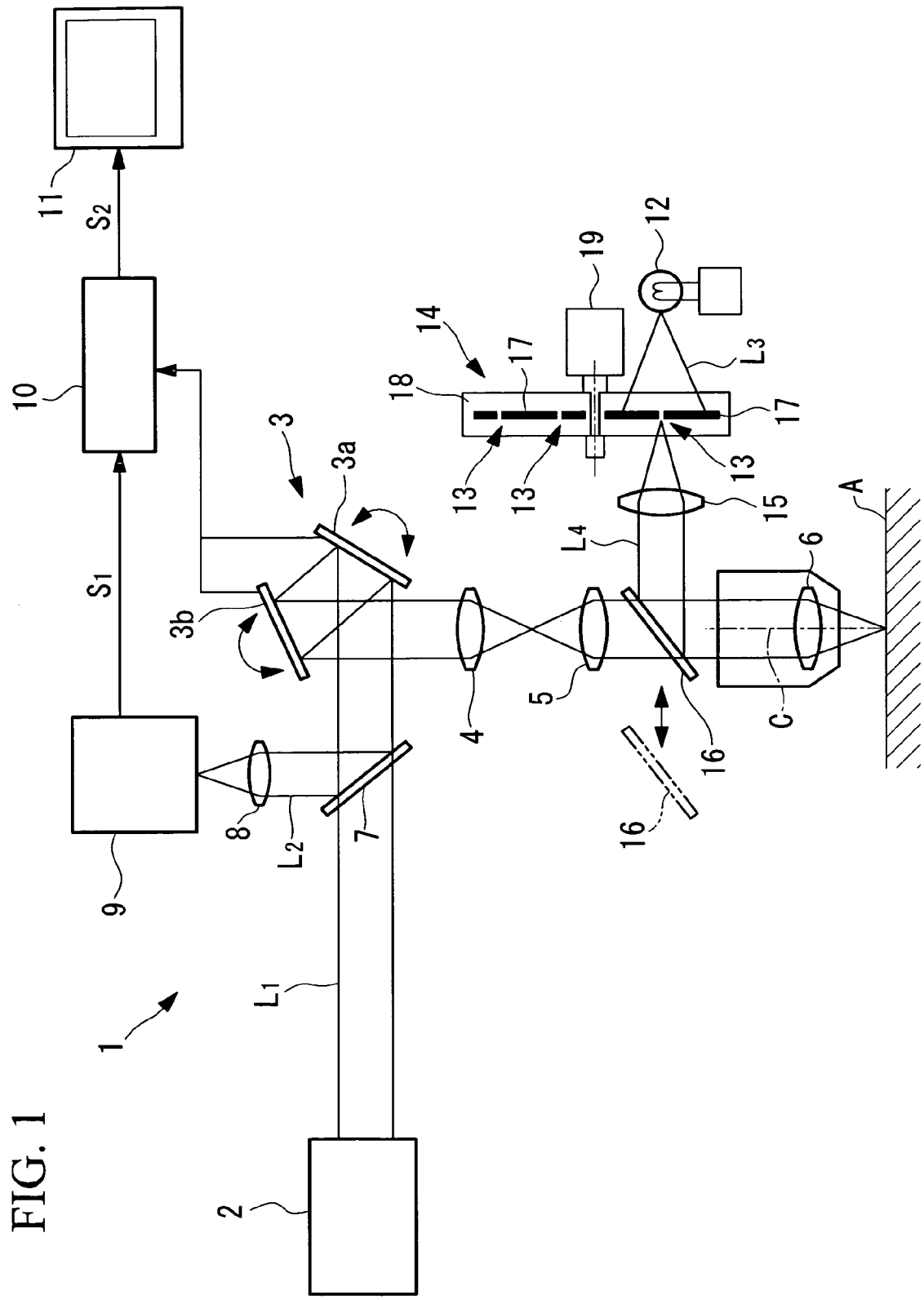
FIG. 1 is a diagram showing the overall configuration of a scanning examination apparatus according to a first embodiment of the present invention.

As shown in FIG. 1, the scanning examination apparatus 1 according to this embodiment, which is a laser-scanning fluorescence microscope apparatus, includes a laser light source (first light source) 2 for emitting laser light $L_1$; a scanner (light scanning unit) 3 for two-dimensionally scanning the laser light $L_1$ emitted from the laser light source 2; a pupil-projection lens 4 for focusing the laser light $L_1$ scanned by the scanner 3 to form an intermediate image; an image-forming lens 5 for collecting the laser light $L_1$ forming the intermediate image and converting it to a substantially collimated beam; and an objective lens 6 for re-imaging the laser light $L_1$ collected by the image-forming lens 5 at a specimen A.

The scanner 3 is formed of so-called proximity galvanometer mirrors in which galvanometer mirrors 3a and 3b, which are provided so as to be rockable about two axes disposed in mutually orthogonal directions, are provided opposite each other (in FIG. 1, the galvanometer mirrors 3a and 3b are illustrated schematically). The objective lens 6 is, for example, a low-magnification objective lens 6 requiring a comparatively large working distance from the specimen A.

The scanning examination apparatus 1 according to this embodiment also includes a dichroic mirror 7, a focusing lens 8, a photodetector (light detecting unit) 9, a signal processing apparatus 10, and a monitor 11. The dichroic mirror 7 splits off fluorescence $L_2$ generated by exciting a fluorescent material included in the specimen A with the laser light $L_1$ and returning via the objective lens 6, the image-forming lens 5, the pupil-projection lens 4, and the scanner 3 from the laser light $L_1$. The focusing lens 8 focuses the fluorescence $L_2$ that has been split off. The photodetector 9 detects the focused fluorescence $L_2$. The signal processing apparatus 10 processes an electrical signal $S_1$ generated in the photodetector 9 by photoelectric conversion and forms an image signal $S_2$. The monitor 11 displays the formed image signal $S_2$.

The photodetector 9 is, for example, a zero-dimensional photomultiplier tube (PMT). Therefore, the photodetector 9 detects the electrical signal $S_1$, which is proportional to the intensity of the fluorescence $L_2$ detected at each instant in time. The signal-processing apparatus 10 determines the intensity of the fluorescence $L_2$ from the electrical signal $S_1$ output from the photodetector 9, determines the position of the fluorescence $L_2$ on the specimen A at each instant in time based on angular information of the galvanometer mirrors 3a and 3b sent from the scanner 3, and combines these pieces of information. Doing so allows it to construct the fluorescence image signal $S_2$.

The scanning examination apparatus according to this embodiment further includes a visible light source 12 for emitting visible light $L_3$, a beam-shaping unit 14, a collimator lens 15, and a mirror 16. By passing the emitted visible beam $L_3$ through a slit 13, the beam-shaping unit 14 shapes it to form a visible light beam $L_4$ having a desired pattern. The collimator lens 15 then converts the shaped visible light beam $L_4$ into a collimated beam. When the mirror 16 is inserted into the optical axis C between the image-forming lens 5 and the objective lens 6, it deflects the collimated visible light beam $L_4$ parallel to the optical axis C of the objective lens 6 and makes it incident on the objective lens 6.

Figure 2A:
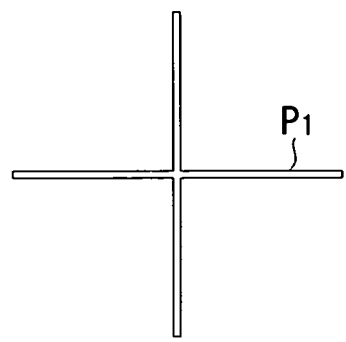
FIG. 2A shows an example of a visible light beam pattern formed by a beam shaping unit in the scanning examination apparatus in FIG. 1.
Figure 2B:
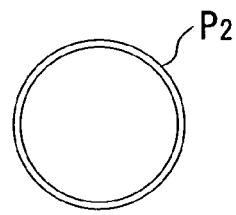
FIG. 2B shows an example of a visible light beam pattern formed by a beam shaping unit in the scanning examination apparatus in FIG. 1.
Figure 2C:
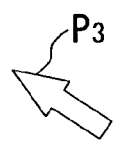
FIG. 2C shows an example of a visible light beam pattern formed by a beam shaping unit in the scanning examination apparatus in FIG. 1.

As shown in FIGS. 2A, 2B, and 2C, for example, the beam-shaping unit 14 is formed of a turret 18 including a plurality of slit plates 17 having slits 13 with a plurality of patterns $P_1$, $P_2$, and $P_3$, and a motor 19 for rotating the turret 18. The turret 18 is rotated by operating the motor 19 to select one of the patterns $P_1$, $P_2$, and $P_3$ to be positioned in the optical path of the visible light $L_3$, which allows the visible light beam $L_4$ to be shaped to the desired pattern $P_1$, $P_2$, or $P_3$.

For example, by selecting the pattern $P_1$ in FIG. 2A, which is a cross-shaped pattern formed of two intersecting straight lines, so that the optical axis C of the objective lens 6 is aligned with the intersection point, an operator who carries out preparations can easily and accurately confirm the position of the optical axis C of the objective lens 6 using the intersecting point in an image of the visible light beam $L_4$ formed on the specimen A. Furthermore, by selecting the pattern $P_2$ in FIG. 2B, which is a circular pattern, so that the optical axis C of the objective lens 6 is aligned with the center of the pattern $P_2$, the operator can confirm that the optical axis C of the objective lens 6 is disposed at the central position of the image of the visible light beam $L_4$ formed on the specimen.

By selecting the pattern $P_3$ in FIG. 2C, which is an arrow shaped pattern, so that the optical axis C of the objective lens 6 is aligned with the tip of the arrow, it is possible to indicate the position of the optical axis C of the objective lens 6 using the arrow-shaped pattern $P_3$.

Therefore, by adjusting the relative positional relationship between the objective lens 6 and the specimen A so that the site to be examined is aligned with the position of the optical axis C of the objective lens 6 indicated by the visible light beam $L_4$ of each pattern $P_1$, $P_2$, and $P_3$, the operator can quickly and accurately position the objective lens 6 relative to the specimen A.

As indicated by the arrow in FIG. 1, the mirror 16 is disposed on the optical axis C between the image-forming lens 5 and the objective lens 6 in such a manner that it can be inserted and removed. When operating the visible light source 12 to make the visible light beam $L_4$ incident on the specimen A, as shown by the solid line in FIG. 1, the mirror 16 is inserted into the optical axis between the image-forming lens 5 and the objective lens 6. On the other hand, when the laser light source 2 is operated to make the laser light $L_1$ incident on the specimen A, as shown by the two-dot chain line in FIG. 1, the mirror 16 is removed from the optical axis between the image-forming lens 5 and the objective lens 6.

The operation of the scanning examination apparatus 1 according to this embodiment, having such configuration, will be described below.

To carry out examination of the specimen A using the scanning examination apparatus 1 according to this embodiment, first, the objective lens 6 is positioned with respect to the specimen A in a preparation stage.

In this case, while the laser light source 2 is turned off, the visible light source 12 is operated and the mirror 16 is inserted into the optical axis C between the image-forming lens 5 and the objective lens 6. Furthermore, by operating the motor 19, the turret 18 is rotated to select one of the slit plates 17 having the slit 13 with the desired pattern $P_1$, $P_2$, or $P_3$. Accordingly, upon transmission through the selected slit plate 17, the visible light L3 emitted from the visible light source 12 is shaped to form the visible light beam $L_4$ having the desired pattern $P_1$, $P_2$, or $P_3$, is converted to a collimated beam by the collimator lens 15, and is incident on the mirror 16. Because the mirror 16 is inserted in the optical axis C between the image-forming lens 5 and the objective lens 6, the visible light beam $L_4$ is deflected and becomes incident on the objective lens 6, and is then imaged onto the surface of the specimen A by the objective lens 6.

Figure 3:
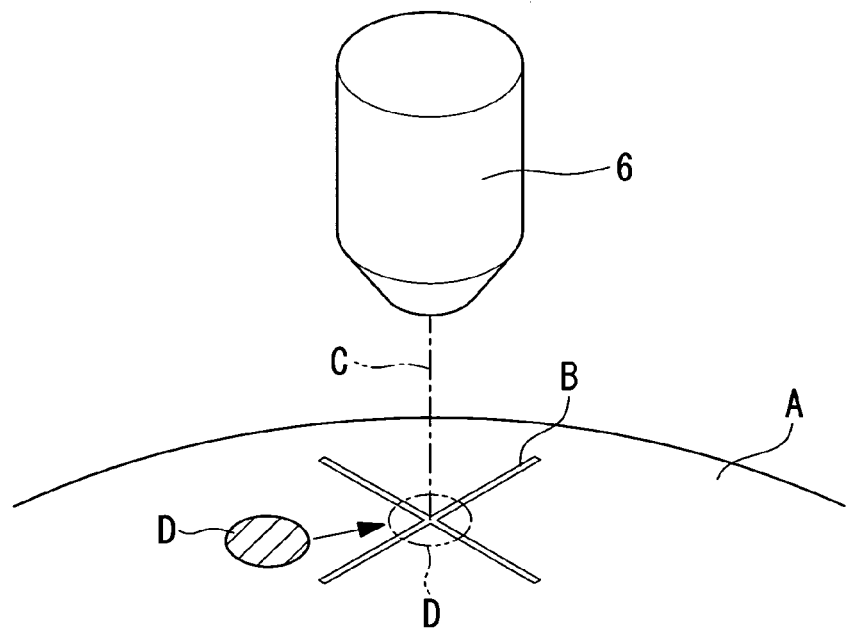
FIG. 3 is a perspective view showing an objective lens, a specimen, and an example of the image of a visible light beam formed at the specimen, in the scanning examination apparatus in FIG. 1.

When the slit plate 17 having the slit 13 with the shape shown, for example, in FIG. 2A is selected, a cross-shaped image B is formed on the surface of the specimen A, as shown in FIG. 3. While the operator observes the image B of the cross-shaped visible light beam $L_4$ imaged on the surface of the specimen A, he or she moves the main body of the scanning examination apparatus 1, including the objective lens 6, relative to the specimen A. Alternatively, by horizontally moving the stage on which the specimen A is mounted, he or she can align the specimen so that a site D to be observed on the specimen A, indicated by the solid line, becomes coincident with the image B of the visible light beam $L_4$, as indicated by the broken line.

Since the apparatus is aligned so that the optical axis C of the objective lens 6 becomes coincident with the intersection of the two straight lines in the image B of the visible light beam $L_4$, by making the image B of the visible light beam $L_4$ coincident with the site D to be examined, it is possible to easily position the site D to be examined at the center of the observation region.

If the image B of the visible light beam $L_4$ on the surface of the specimen A is unclear, this means that the gap between the objective lens 6 and the specimen A does not match the working distance. In such a case, by moving the objective lens 6 relative to the specimen A in the direction of the optical axis C to set the image B of the visible light beam $L_4$ at a position where it becomes most clear, it is possible to align the image position of the visible light beam $L_4$ emitted from the objective lens 6 with the surface of the specimen A.

By doing so, the optical axis C of the objective lens 6 can be aligned with the examination site D on the specimen A, and the distance between the objective lens 6 and the specimen A can be made to match the working distance. This completes the preparation stage.

Next, in order to examine the specimen A, operation of the visible light source is stopped, and the mirror 16 is removed from between the image-forming lens 5 and the objective lens 6. In this state, the laser light source 2, the scanner 3, and the photodetector 9 are operated, and the laser light L1 emitted from the laser light source 2 is scanned on the specimen A. Thus, a fluorescent material in the specimen A is excited to emit fluorescence L2, and this emitted fluorescence L2 is detected by the photodetector 9.

The fluorescence image signal S2 is then produced in the signal processing apparatus 10 and is displayed on the monitor 11.

According to the scanning examination apparatus 1 of this embodiment, because the optical axis C of the objective lens can be correctly aligned with the examination site D in the specimen A during the preparation stage, a fluorescence image to be observed can be quickly acquired in the examination stage. Therefore, it is possible to reduce the time required for all examination steps, including those in the preparation stage. Also, if the scanning examination apparatus is a confocal microscope, because the imaging position of the laser light L1 formed by the objective lens 6 is set to be aligned with the surface of the specimen A after the preparation stage is completed, it is possible to acquire a fluorescence image at a desired depth position by moving the objective lens 6 in the direction of the optical axis C, using that imaging position as a reference.

With the scanning examination apparatus 1 according to this embodiment, slit plates 17 with a plurality of patterns $P_1$, $P_2$, and $P_3$ are attached to the turret 18. Therefore, in the preparation stage prior to examination using this scanning examination apparatus 1, if the image B of the visible light beam $L_4$ to be formed at the surface of the specimen A is not aligned with the specimen A, the turret 18 is rotated by operating the motor 19, which allows the most suitable pattern to be selected from among the patterns $P_1$, $P_2$, and $P_3$. For example, with a pattern that directly indicates the position of the optical axis C of the objective lens 6 using an intersection point, like the cross-shaped pattern $P_1$ shown in FIG. 2A, when the surface of the specimen A has a complicated shape at the position of this intersection point, the image B becomes degraded. Therefore, as shown in FIG. 2B, in some cases it is preferable to indicate the position of the optical axis C of the objective lens 6 using the circular pattern $P_2$, which surrounds the examination site.

In this embodiment, the visible light $L_3$ from the visible light source 12 is merely shaped and then directly irradiated onto the specimen A. Instead of this, however, a plurality of switchable visible light sources 12 that can emit visible light $L_3$ with different wavelengths may be provided, and one of these visible light sources 12 may be selected to match the surface color of the specimen A. With this configuration, the image B of the visible light beam $L_4$ formed on the surface of the specimen A can be discriminated, which facilitates positioning of the optical axis C of the objective lens 6.

For example, when the surface of the specimen A is red, irradiating a red visible light beam L4 makes it impossible to discern the image B of the visible light beam $L_4$ formed on the surface of the specimen A. In this case, it is preferable to switch to the visible light source 12 that emits visible light of a wavelength that allows the image B to be discerned, such as green light.

Next, a scanning examination apparatus 20 according to a second embodiment of the present invention will be described below with reference to FIGS. 4 and 5.

In the description of this embodiment, parts having the same configuration as those in the scanning examination apparatus 1 according to the first embodiment described above are assigned the same reference numerals, and a description thereof shall be omitted.

Figure 4:
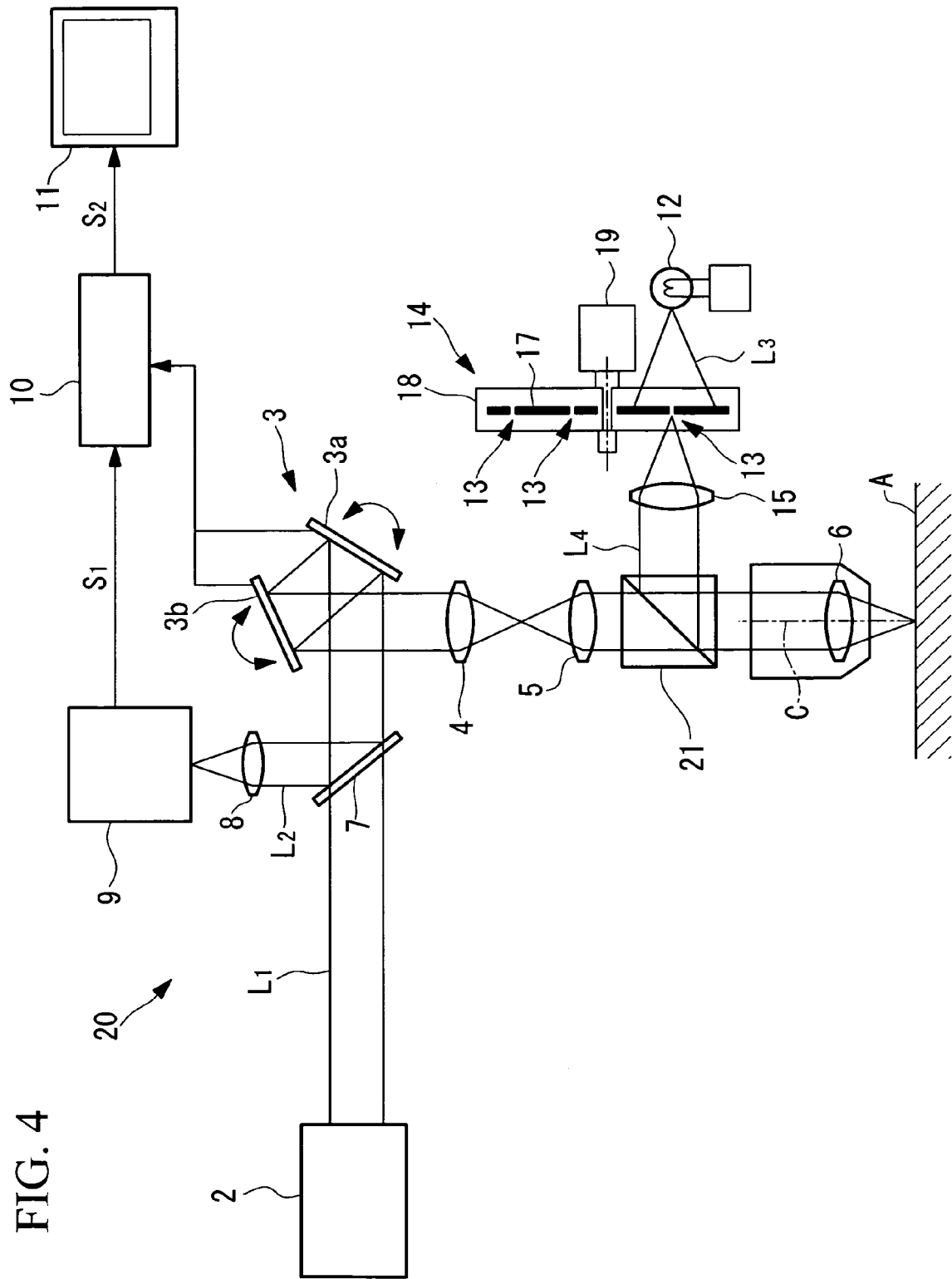
FIG. 4 is a diagram showing the overall configuration of a scanning examination apparatus according to a second embodiment of the present invention.

The scanning examination apparatus 20 according to this embodiment differs from the first embodiment in that, instead of the mirror 16 in the scanning examination apparatus 1 according to the first embodiment, a half-mirror 21 is permanently disposed between the image-forming lens 5 and the objective lens 6, as shown in FIG. 4.

The operation of the scanning examination apparatus 20 according to this embodiment, having such a configuration, will be described below.

With the scanning examination apparatus 20 according to this embodiment, during a preparation stage, when the laser light source 2 is turned off and the visible light source 12 is operated to emit the visible light beam $L_4$, which is shaped with the desired pattern P1, P2, or P3, the visible light beam $L_4$ is deflected by the half-mirror 21 in the direction of the optical axis C of the objective lens 6 and is imaged at the surface of the specimen A by the objective lens 6. While the operator observes the image B of the visible light beam $L_4$ on the specimen A, he or she can align the optical axis C of the objective lens 6 so that it is coincident with the examination site D on the specimen A, similarly to the first embodiment described above.

With the scanning examination apparatus 20 according to this embodiment, by operating the scanner 3, the photodetector 9, the signal processing apparatus 10, and the monitor 11 during the preparation stage, the visible light beam $L_4$ imaged at the surface of the specimen A is reflected therefrom and returns to the objective lens 6. It is then transmitted through the half-mirror 21, travels via the image-forming lens 5, the pupil projection lens 4, the scanner 3, the dichroic mirror 7, and the focusing lens 8, and is detected by the photodetector 9. An image of the visible light $L_3$ formed by the signal processing apparatus 10 is then displayed on the monitor 11.

Figure 5:
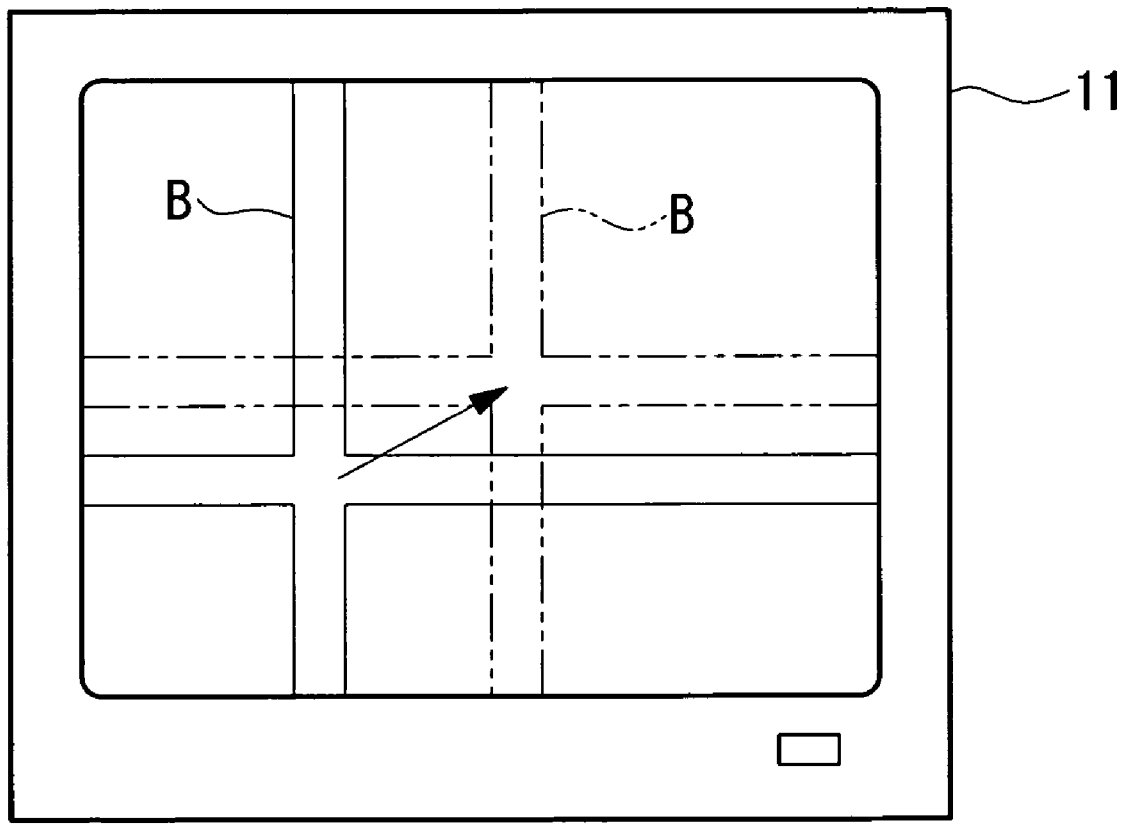
FIG. 5 illustrates a visible light beam image displayed on a monitor of the scanning examination apparatus in FIG. 4.

In other words, as shown by the solid line in FIG. 5, the image B of the visible light beam $L_4$ on the surface of the specimen A can be expanded and observed on the monitor 11. At this time, as shown by the solid line in FIG. 5, if the image B of the surface of the specimen A is displaced on the monitor 11, the optical axis C of the objective lens 6 is shifted relative to the scanning region of the scanner 3. Therefore, by adjusting the angular range of the rocking motion of the galvanometer mirrors 3a and 3b constituting the scanner 3, it is possible to align the position of the optical axis C of the objective lens 6 substantially at the center of the scanning region, as shown by the two-dot chain line in FIG. 5. This completes the preparation stage.

Thereafter, by turning off the visible light source 12 and operating the laser light source 2, the laser light L1 is scanned on the specimen A, which allows a fluorescence image to be obtained. The obtained fluorescence image is an image of the surface of the specimen A corresponding to a scanning region substantially centered on the optical axis C of the objective lens 6; in other words, it is the desired fluorescence image of the center of the examination site D of the specimen A.

Therefore, with the scanning examination apparatus 20 according to this embodiment, in the preparation stage, it is possible to adjust the scanning region of the scanner 3 relative to the position of the optical axis C of the objective lens 6 by aligning the position of the optical axis C of the objective lens 6 with the examination site D of the specimen A using the image B of the visible light beam $L_4$. In addition, it is possible to rapidly acquire the desired image, including the examination site D, during the examination stage.

In each of the embodiments described above, the laser light source 2 is used as the first light source. Instead of this, however, any other light source may be used. More specifically, an excitation light source that emits excitation light may be used, or a light source formed by combining a halogen lamp and an excitation filter may be used.

Furthermore, the invention is not limited to a fluoroscopy apparatus that radiates excitation light and collects the resulting fluorescence.

Although a structure having the slits 13 with the patterns P1, P2, and P3 shown in FIGS. 2A, 2B, and 2C has been described as an example of the slit plates 17 in the beam-shaping unit 14, instead of this, a structure having slits 13 with any other patterns may be employed. In this case, so long as a structure having a shape that directly or indirectly indicates the position of the optical axis C of the objective lens 6 is used, it may have any shape. Furthermore, it is not limited to the slits 13; the visible light beam $L_4$ with the predetermined patterns P1, P2, and P3 may be formed using a digital micromirror device (DMD).

Next, a scanning examination apparatus according to a third embodiment of the present invention will be described below with reference to FIGS. 6 and 7.

The scanning examination apparatus according to this embodiment is a microscope apparatus including the structure of the scanning examination apparatus 1 described in the first embodiment.

More specifically, the scanning examination apparatus of this embodiment includes an examination apparatus main body (not shown in the drawings) and a microscope objective lens unit 101 (see FIG. 6) that is removably attached to the examination apparatus main body.

Figure 6:
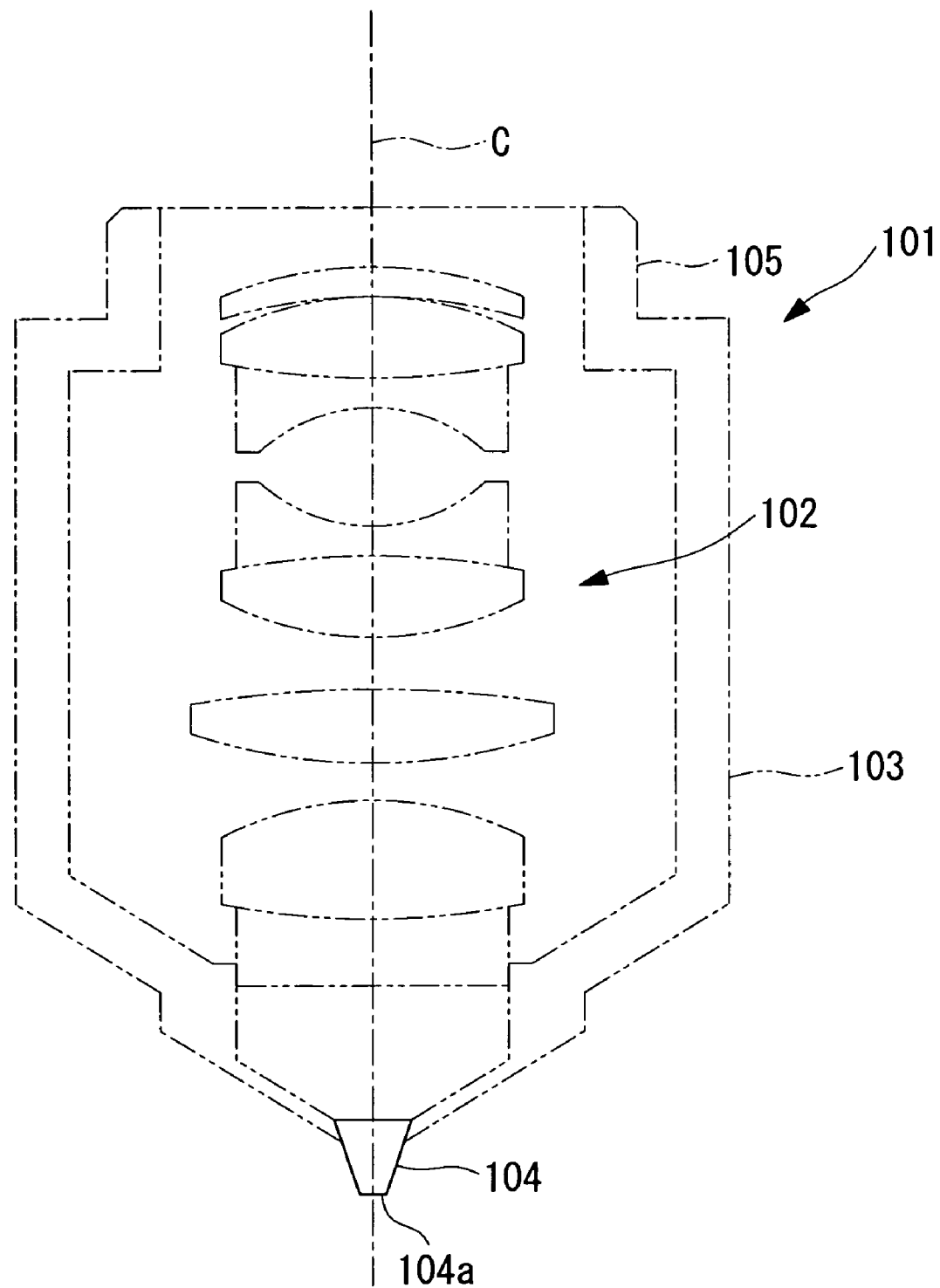
FIG. 6 is a diagram showing a microscope objective lens unit used in a scanning examination apparatus according to a third embodiment of the present invention.
Figure 7:
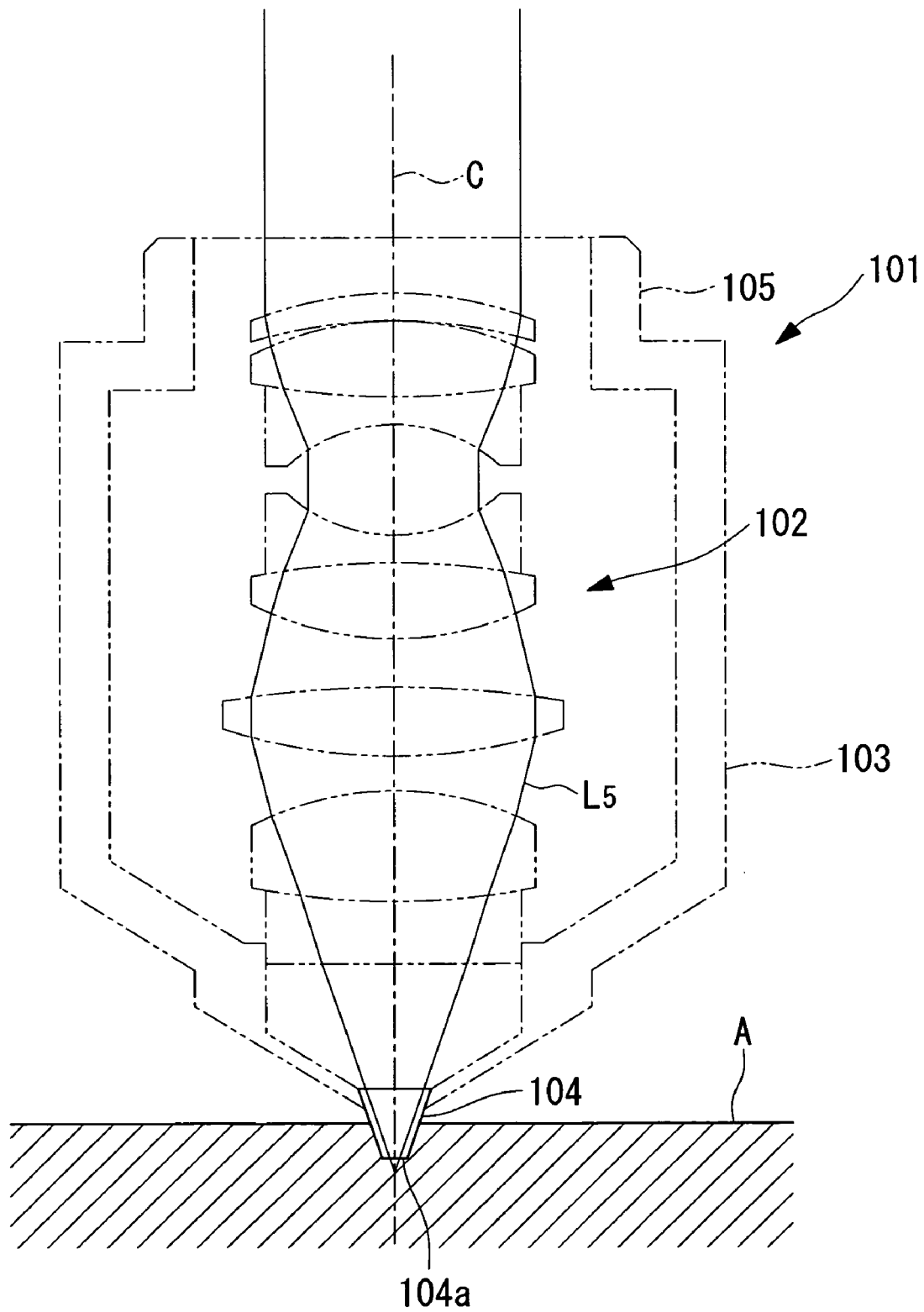
FIG. 7 is a diagram for explaining examination of a specimen using the microscope objective lens unit in FIG. 6.

As shown in FIG. 6, the microscope objective lens unit 101 includes an infinity optical lens group 102 (objective lens 6) formed of a plurality of lenses, a lens barrel 103 for accommodating the infinity optical lens group 102, and a pointed insertion member 104 disposed at the end of the lens barrel 103. The lens barrel 103 is provided with a threaded mount 105 for removably attaching the microscope objective lens unit 101 to the examination apparatus main body (not shown).

The infinity optical lens group 102 is, for example, a low magnification lens group having a magnification of about 4× to 10×, and the working distance thereof is about 10 mm to 16 mm.

The insertion member 104, which is formed of an optically transparent material, for example, glass, protrudes at the tip of the lens barrel 103 parallel to the optical axis C and is formed in the shape of a frustum that progressively tapers towards the tip thereof. A transmissive surface 104a orthogonal to the optical axis C is formed at the end surface of the insertion member 104. Light coming from the examination apparatus main body and entering the microscope objective lens unit 101 passes through this transmissive surface 104a and is emitted.

The transmissive surface 104a at the tip of the insertion member 104 is positioned slightly towards the infinity optical lens group 102 from the focal point of the infinity optical lens group 102. Therefore, illumination light or excitation light coming via the infinity optical lens group 102 is arranged to pass through the insertion member 104, be emitted from the transmitting surface 104a, and form an image slightly outside the transmissive surface 104a.

With the scanning examination apparatus according to this embodiment, having such a configuration, by attaching the microscope objective lens unit 101 to the examination apparatus main body, it is possible to dispose the insertion member 104 so that it extends along the optical axis C of the examination apparatus main body. Therefore, as shown in FIG. 7, the insertion member 104 punctures the surface of the specimen A to be examined, such as a biological specimen, and the transmissive surface 104a is disposed below the surface of the specimen A.

In this state, an illumination light source or an excitation light source (laser light source 2) provided in the examination apparatus main body is operated, and illumination light or excitation light $L_5$ is guided inside the microscope objective lens unit 101, is emitted from the transmissive surface 104a at the tip of the insertion member 104, and is imaged outside the transmissive surface 104a. Accordingly, the illumination light or excitation light L5 is irradiated at an examination site disposed below the surface of the specimen A, and reflected light or fluorescence therefrom can return inside the microscope objective lens unit 101 from the transmissive surface 104a at the tip of the insertion member 104.

With the scanning examination apparatus according to this embodiment, because the insertion member 104 of the microscope objective lens unit 101 is formed to have a diameter small enough to allow penetration of the specimen A, there is no need to make a large incision in the specimen A, even though the outer diameter of the lens barrel 103 of the microscope objective lens unit 101 is large. This provides an advantage in that it is possible to examine below the surface of the specimen A with minimal invasiveness.

Here, the scanning examination apparatus according to this embodiment is a microscope apparatus having the structure of the scanning examination apparatus 1 described in the first embodiment. It is not limited to this, however, and may also be a microscope apparatus having the scanning examination apparatus structure described in the second embodiment.

Next, a scanning examination apparatus according to a fourth embodiment of the present invention will be described below with reference to FIGS. 8 and 9.

In the description of this embodiment, parts having the same configuration as those of the scanning examination apparatus according to the third embodiment described above are assigned the same reference numerals, and a description thereof shall be omitted.

The scanning examination apparatus according to this embodiment uses a microscope objective lens unit 110 instead of the microscope objective lens unit 101 in the scanning examination apparatus described in the third embodiment. The microscope objective lens unit 110 differs from the microscope objective lens unit 101 according to the first embodiment in terms of the structure of an insertion member 111.

Figure 8:
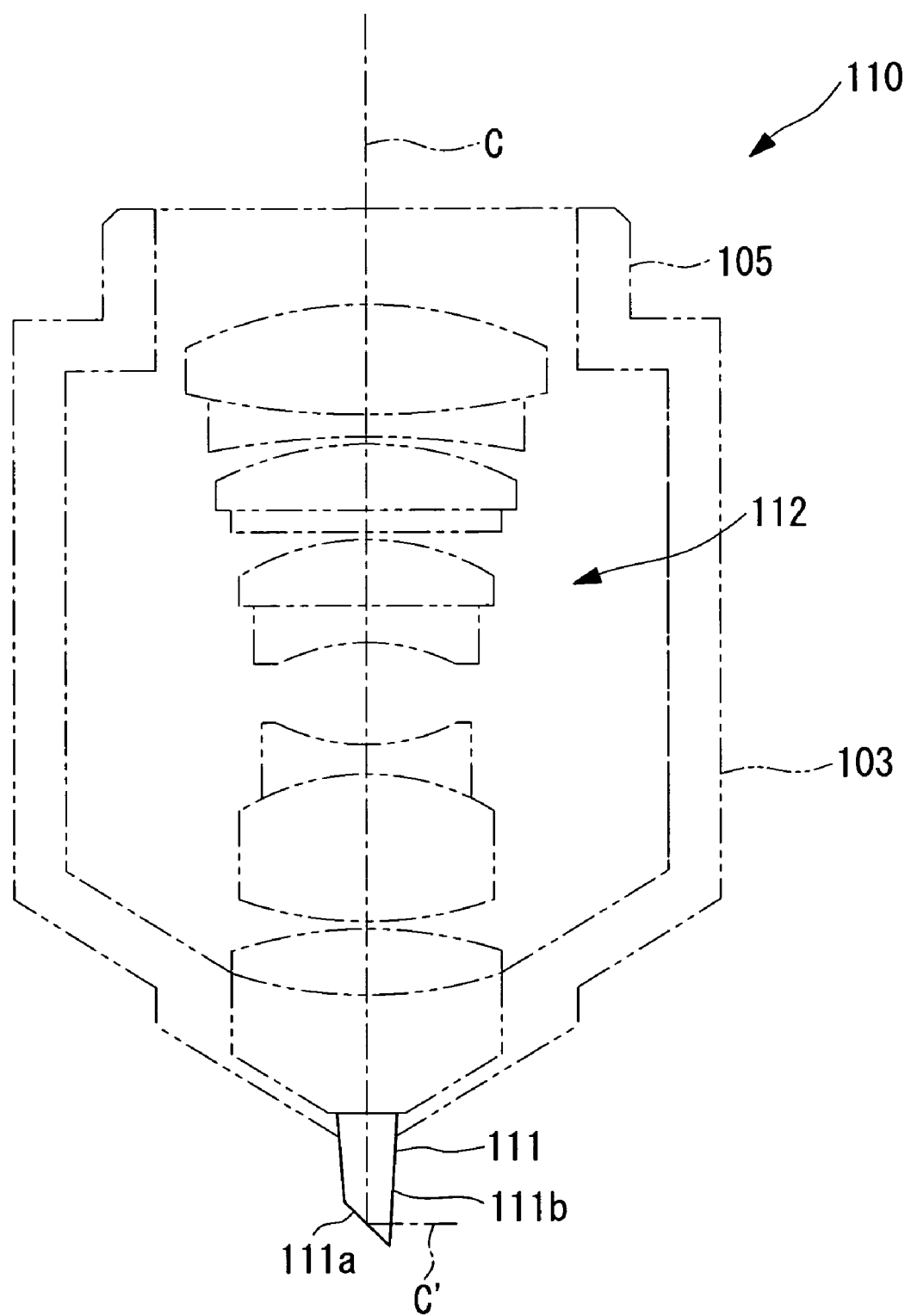
FIG. 8 is a diagram showing a microscope objective lens unit used in a scanning examination apparatus according to a fourth embodiment of the present invention.
Figure 9:
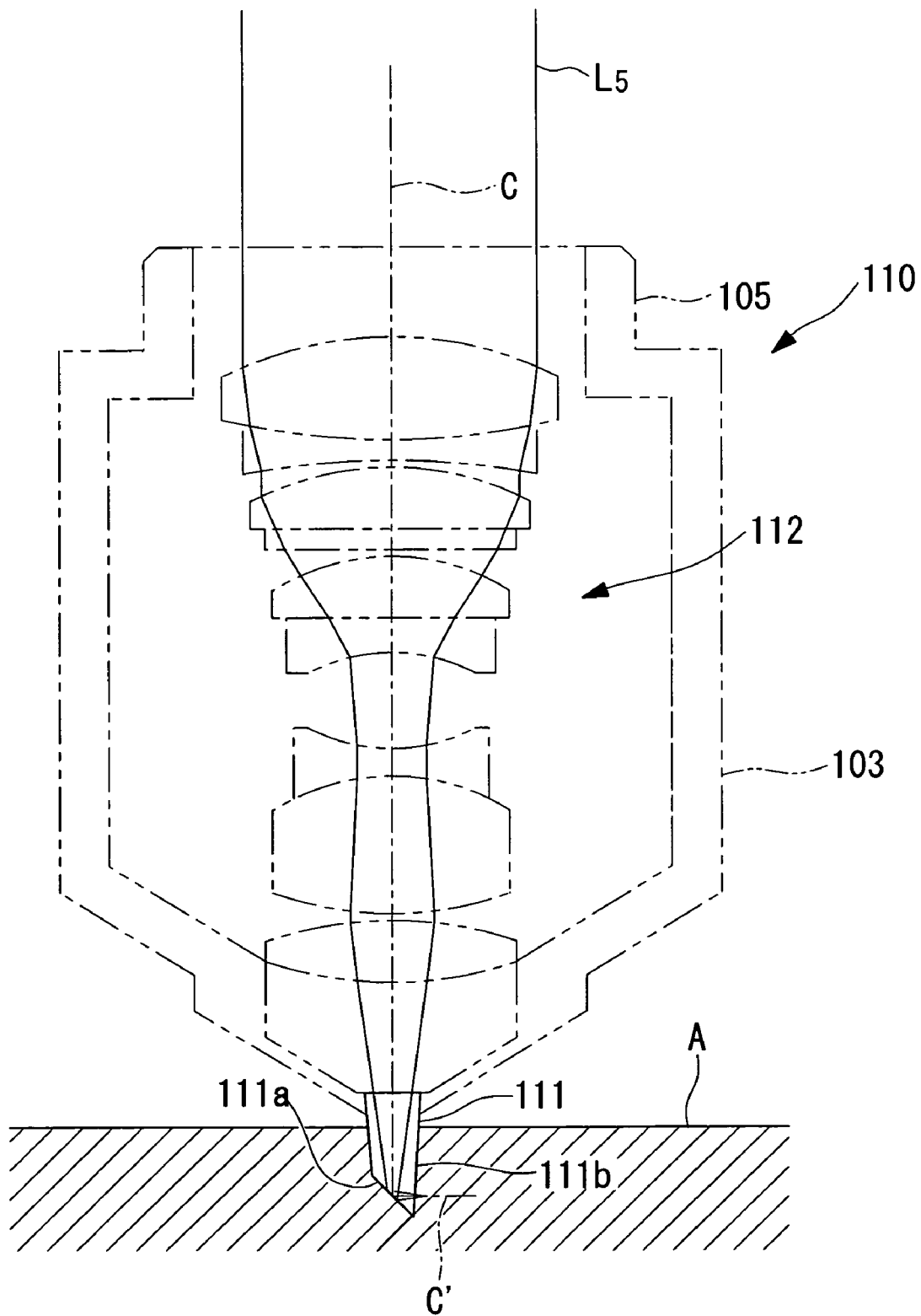
FIG. 9 is a diagram for explaining examination of a specimen using the microscope objective lens unit in FIG. 8.

As shown in FIG. 8, the insertion member 111 in this embodiment has, at the tip thereof, a reflecting surface 111a inclined at an angle of substantially 45° with respect to the optical axis C of an infinity optical lens group 112.

Accordingly, the optical axis C extending from the infinity optical lens group 112 is bent by an angle of substantially 90° at the reflecting surface 111a. Also, the insertion member 111 is provided with a transmissive surface 111b which is orthogonal to an optical axis C' bent by substantially 90° by the reflecting surface 111a. With this configuration, illumination light or excitation light $L_5$ coming from the infinity optical lens group 112 is bent by substantially 90° at the reflecting surface 111a at the tip of the insertion member 111 and, thereafter, passes through the transmissive surface 111b and is imaged outside the transmissive surface 111b.

With the scanning examination apparatus according to this embodiment, having such a configuration, by attaching the microscope objective lens unit 110 to the examination apparatus main body, it is possible to dispose the insertion member 111 such that it extends along the optical axis C of the examination apparatus main body. Then, as shown in FIG. 9, the insertion member 111 punctures the surface of the specimen to be examined, such as a biological specimen, and the tip thereof is disposed below the surface of the specimen A.

When an illumination light source or an excitation light source provided in the examination apparatus main body is operated in this state, and illumination light or excitation light $L_5$ is guided inside the microscope objective lens unit 110 and is introduced into the insertion member 111, and the illumination light or excitation light L5 is reflected by the reflecting surface 111a provided at the tip of the insertion member 111 and is emitted from the transmissive surface 111b disposed in the side surface of the insertion member 111. The focal position of the infinity optical lens group 112 in the microscope objective lens unit 110 is on the outer side close to the transmissive surface 111b. Therefore, the illumination light or excitation light $L_5$ is imaged outside the transmissive surface 111b and irradiates an examination site disposed below the surface of the specimen A. Reflected light or fluorescence therefrom can return inside the microscope objective lens unit 110 through the transmissive surface 111b at the tip of the insertion member 111.

With the scanning examination apparatus according to this embodiment, the insertion member 111 of the microscope objective lens unit 110 punctures the specimen A and enables examination in a direction orthogonal to the puncturing direction. Furthermore, in the present embodiment, the insertion member 111 is formed to have a diameter that is sufficiently small relative to the lens barrel 103.

Therefore, it is not necessary to make a large incision in the specimen A, even though the outer dimensions of the lens barrel 103 of the microscope objective lens unit 110 are large. This provides an advantage in that it is possible to carry out minimally invasive examination below the surface of the specimen A in a direction parallel to the surface.

Next, a scanning examination apparatus according to a fifth embodiment of the present invention will be described below with reference to FIG. 10.

The scanning examination apparatus according to this embodiment is a microscope apparatus including the structure of the scanning examination apparatus 1 described in the first embodiment.

More specifically, the scanning examination apparatus according to this embodiment includes an examination apparatus main body (not shown in the drawings), a microscope objective lens unit 101' provided on this examination apparatus main body, and an objective-lens adaptor 120 attached to the end of this microscope objective lens unit 101'.

The microscope objective lens unit 101' is provided with a structure (male threaded portion 122, described below) for attaching the objective-lens adaptor 120, instead of the insertion member 104 on the microscope objective lens unit 101 shown in the third embodiment described above.

Figure 10:
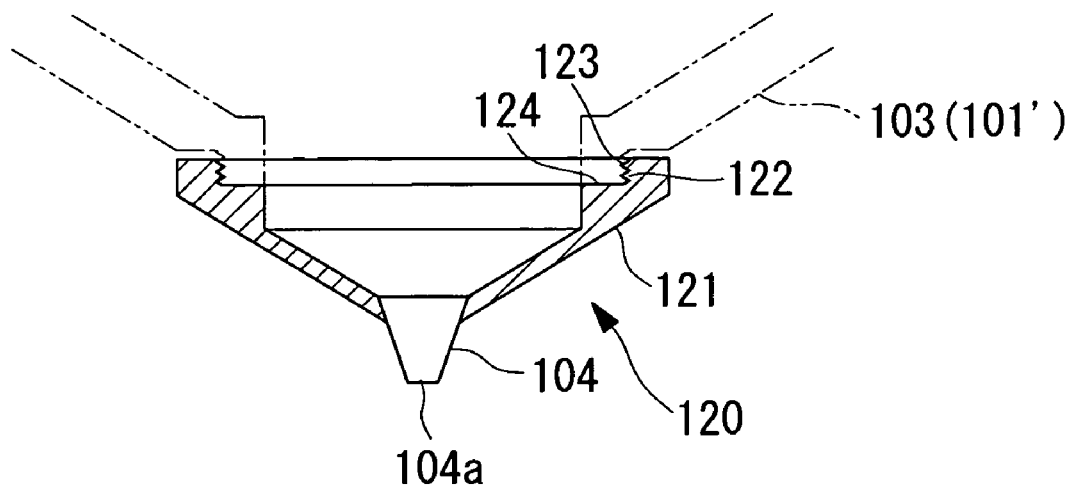
FIG. 10 is a longitudinal sectional view showing an objective-lens adaptor used in a scanning examination apparatus according to a fifth embodiment of the present invention.

As shown in FIG. 10, the objective-lens adaptor 120 according to this embodiment includes an insertion member 104, like that provided at the end of the microscope objective lens unit 101 according to the third embodiment, and a mounting portion 121 for securing the insertion member 104.

As shown in FIG. 10, the mounting portion 121, which is a substantially conical member for securing the insertion member 104, includes a female threaded portion 123 for engaging with the male threaded portion 122 provided at the end of the lens barrel 103 of the microscope objective lens unit 101', and also includes an abutting portion 124 that abuts against the end face of the lens barrel 103. By engaging the female threaded portion 123 of the mounting portion 121 with the male threaded portion 122 provided at the end of the lens barrel 103 of the microscope objective lens unit 101' until the abutting portion 124 abuts against the end face of the lens barrel 103, the insertion member 104 is secured in an aligned state with respect to the infinity optical lens group 102 of the microscope objective lens unit 101'.

With the objective-lens adaptor 120 according to this embodiment, having the above-described configuration, by attaching it in an aligned state to the end of the microscope objective lens unit 101', it is possible to set the focal position of the infinity optical lens group 102 of the microscope objective lens unit 101' slightly outside the transmissive surface 104a at the tip of the insertion member 104.

Therefore, simply by attaching the objective-lens adaptor 120 according to this embodiment to the end of the standard objective lens unit 101' having the male threaded portion 122 at the end thereof, it is possible for the microscope objective lens unit 101' to puncture the specimen A to examine the conditions below the surface.

Here, the scanning examination apparatus according to this embodiment is a microscope apparatus having the structure of the scanning examination apparatus 1 described in the first embodiment. Instead of this, however, it may be a microscope apparatus having the structure of the scanning examination apparatus described in the second embodiment.

Figure 11:
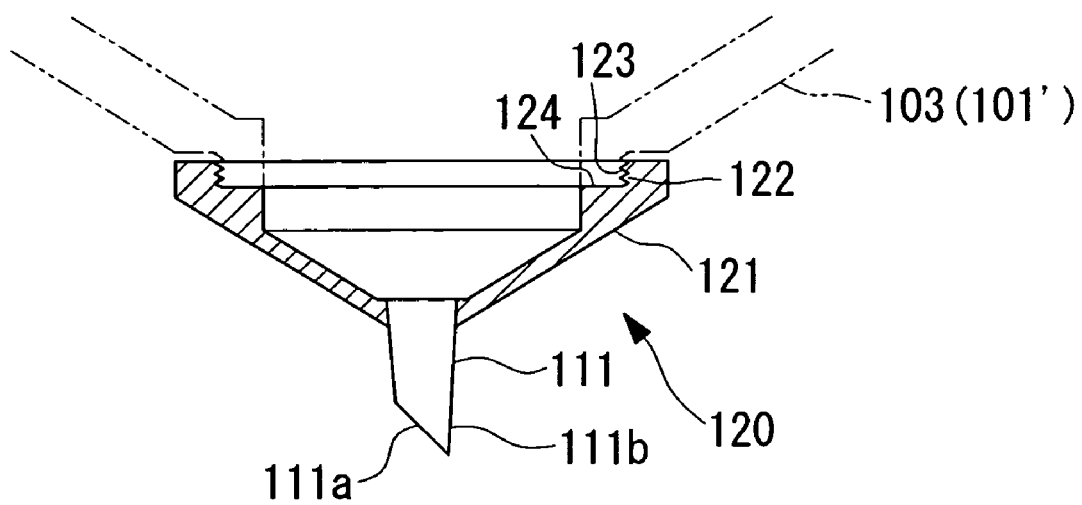
FIG. 11 is a longitudinal sectional view showing a modification of the objective-lens adaptor in FIG. 10.

In the objective-lens adaptor 120 according to this embodiment, an example has been described in which the transmissive surface 104a of the insertion member 104 is disposed orthogonally to the optical axis C of the infinity optical lens group 102 in the microscope objective lens unit 101'. Instead of this configuration, as shown in FIG. 11, it is possible to provide an insertion member 111 with a structure including a reflecting surface 111a at the tip thereof that bends the optical axis by 90°, like the insertion member 111 of the microscope objective lens unit 110 according to the second embodiment.

Figure 12:
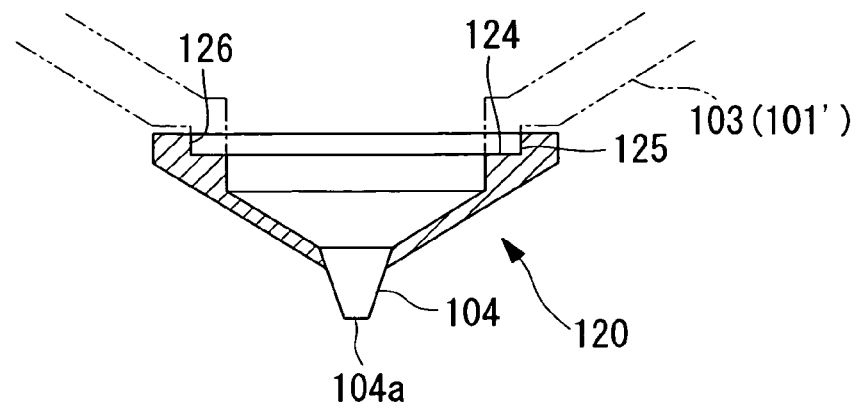
FIG. 12 is a longitudinal sectional view showing another modification of the objective-lens adaptor in FIG. 10.

In the embodiment described above, the objective-lens adaptor 120 with a structure for attaching by engaging with the threaded portion at the end of the microscope objective lens unit 101' has been described by way of example. Instead of this structure, however, as shown in FIG. 12, the objective-lens adaptor 120 may include a tubular mating portion 126 for mating with a cylindrical surface 125 provided at the end of the lens barrel 103 of the microscope objective lens unit 101', or it may be secured to the lens barrel 103 by another method, such as an adhesive or a magnet.

In the embodiment described above, a lens barrel having a large outer diameter, serving as the microscope objective lens unit, has been described. Instead of this, however, if the outer diameter of the portion at the end of the lens barrel can be made comparatively small, there are cases where it is desirable to switch the observation direction between the direction along the optical axis and the direction orthogonal thereto.

Figure 13:
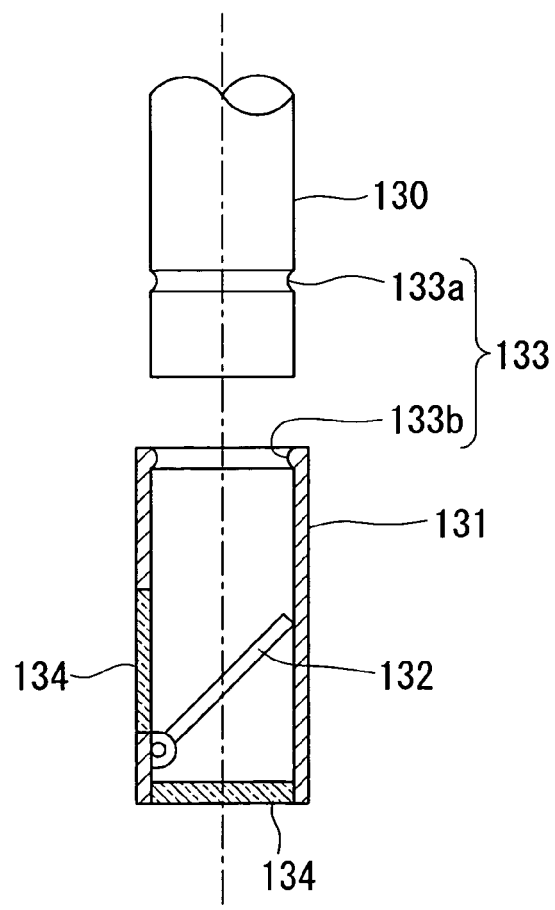
FIG. 13 is a longitudinal sectional view showing a modification of an adaptor for attachment to the end of a lens barrel in the microscope objective lens unit.

In such a case, as shown in FIG. 13, an adaptor 131 is attached to the end of a lens barrel 130. The adaptor 131 contains a reflecting plate 132 whose angle can be changed, and an attaching structure 133 is provided for attaching the adaptor 131 to the end of the lens barrel 130 by a simple pushing operation. Windows 134 formed of an optically transparent material, for example, glass, are provided in the end surface and the side surface of the adaptor 131. In the example shown in FIG. 13, the attaching structure 133 is formed of a circumferential groove 133a provided in the outer surface near the end of the lens barrel 130 and a mating projection 133b, provided in the adaptor 131, for mating with this circumferential groove 133a.

Figure 14:
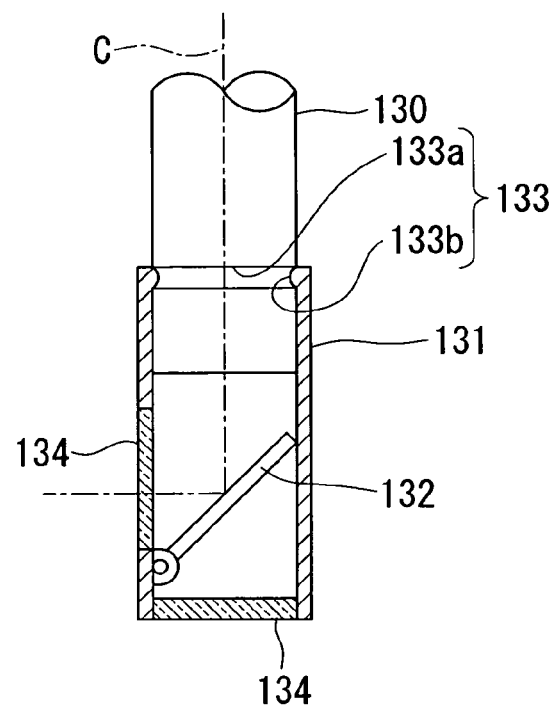
FIG. 14 is a longitudinal sectional view showing the adaptor in FIG. 13 attached to the lens barrel.

As shown in FIG. 14, when the adaptor 131 is attached to the end of the lens barrel 130 using the attaching structure 133 and the reflecting plate 132 is tilted, the optical axis C of the lens barrel 130 is bent by the reflecting plate 132 and is directed towards the window 134 provided in the side surface of the adaptor 131. Accordingly, when the tip of the adaptor 131 punctures a specimen, it is possible to observe the conditions below the specimen surface, which is disposed in a direction orthogonal to the puncturing direction.

Figure 15:
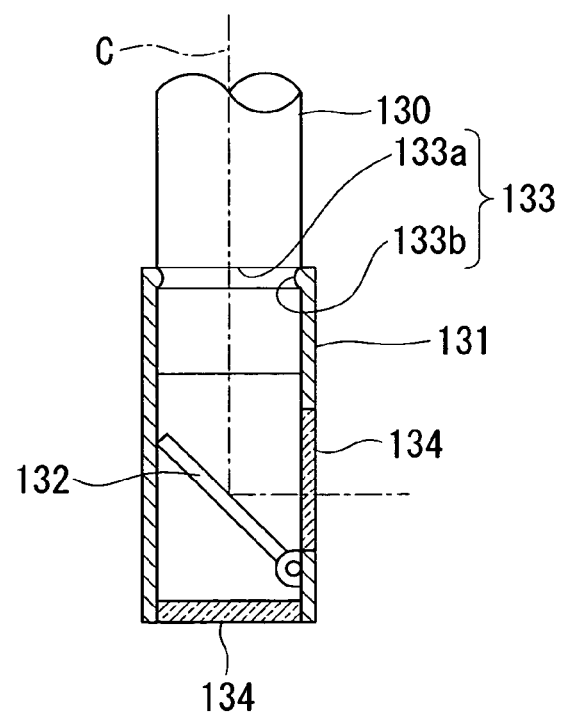
FIG. 15 is a longitudinal sectional view showing the adaptor in FIG. 14 rotated about the optical axis with respect to the lens barrel.

Also, because the attaching structure 133 in this embodiment mates the circumferential groove 133a and the mating projection 133b, as shown in FIG. 15, it is possible to rotate the adaptor about the optical axis C relative to the lens barrel 130. Therefore, it is possible to change the observation direction, which is orthogonal to the optical axis C, around the entire circumference thereof while keeping the lens barrel 130 fixed.

Figure 16:
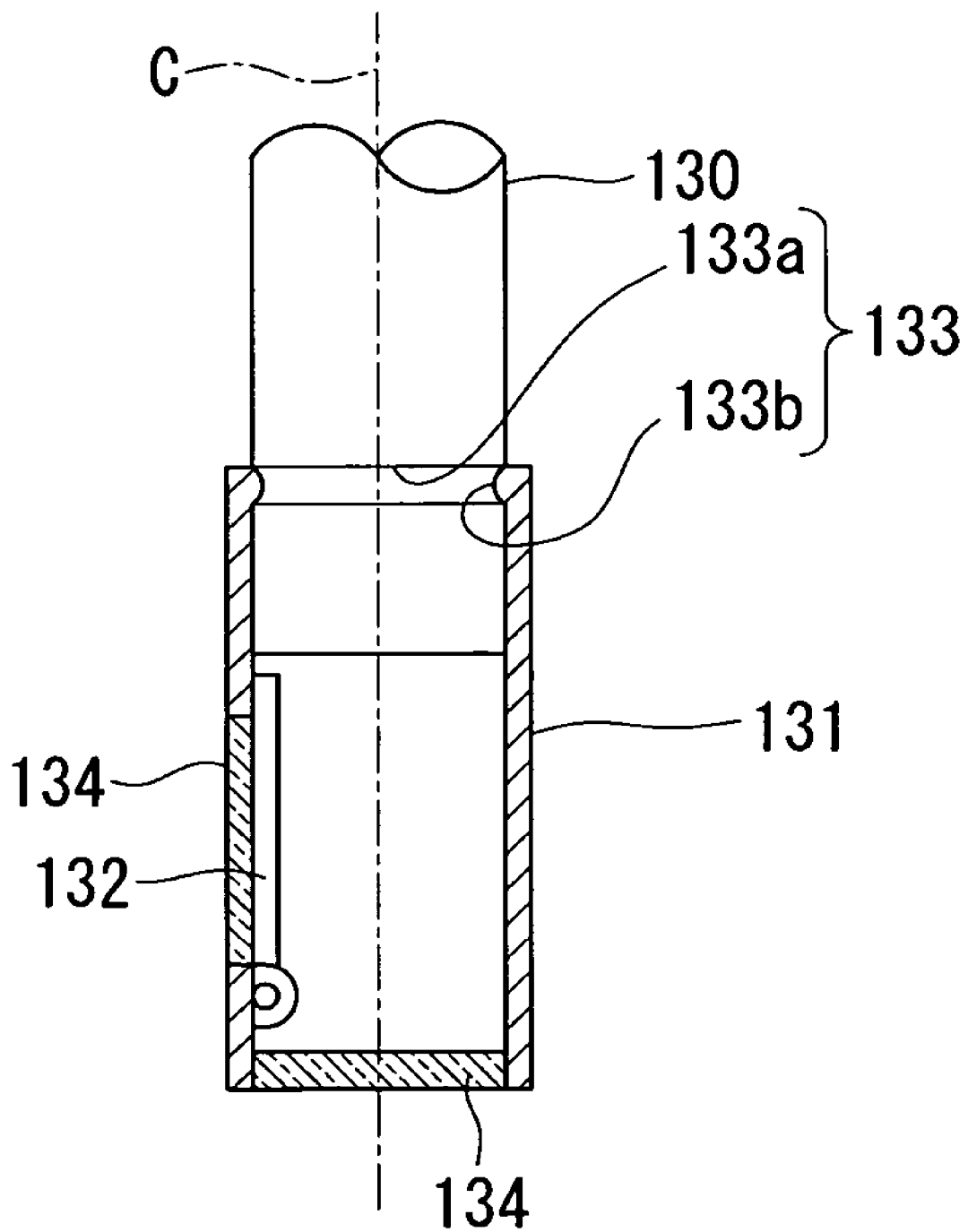
FIG. 16 is a longitudinal sectional view showing a reflector in the adaptor in FIG. 14 in a folded state.

Also, when observation is to be performed in the optical axis direction of the lens barrel 130, as shown in FIG. 16, the reflecting plate 132 is removed from the optical axis C by folding it upwards, which allows observation of the exterior through the window 134 at the tip of the adaptor 131.

Therefore, it is possible to observe the conditions below the specimen surface, which is disposed towards the front in the puncturing direction.

The reflecting plate 132 may move back and forth by pushing and pulling wires (not shown), or it may be driven using any other type of driving mechanism, such as a magnet and so forth.

In the third to fifth embodiments described above, scanning examination apparatuses having an objective lens unit or an objective-lens adaptor have been described, but the invention is not limited to these configurations. If the principal aim is to realize microscope examination that minimizes the invasiveness to the specimen, the objective lens unit or the objective-lens adaptor described above may be attached to a standard microscope apparatus.

What is claimed is:

1. A scanning examination apparatus comprising:
   a first light source;
   a light scanning unit configured to scan light from the first light source on a specimen;
   an objective lens configured to form an image of the light scanned in the light scanning unit at the specimen;
   a light-detecting unit configured to detect return light emitted from the specimen;
   a second light source configured to emit visible light;
   a deflecting optical element, disposed between the light scanning unit and the objective lens, for making visible light emitted from the second light source enter the objective lens along an optical axis of the objective lens; and
   a beam-shaping unit configured to form the visible light from the second light source, which is irradiated onto a surface of the specimen via the objective lens using the deflecting optical element, into a pattern that enables the optical axis of the objective lens to be indicated;
   wherein the deflecting optical element is formed of a mirror and is disposed so as to be insertable in and removable from between the light scanning unit and the objective lens.

2. A scanning examination apparatus according to claim 1, wherein the beam-shaping unit is configured to enable selective switching of the pattern of visible light from the second light source.

3. A scanning examination apparatus according to claim 1, wherein the second light source is a wavelength-switchable light source.

4. A scanning examination apparatus according to claim 1, further comprising:
   an examination apparatus main body;
   a lens unit configured to be removably attached to the examination apparatus main body, the lens unit including the objective lens; and
   a pointed insertion member formed of an optically transparent material, provided at the end of the lens unit to protrude along the optical axis, wherein the focal position of the lens unit is disposed outside the tip of the insertion member.

5. A scanning examination apparatus according to claim 4 further comprising, at a tip of the insertion member, a transmissive surface orthogonal to the optical axis.

6. A scanning examination apparatus according to claim 4 further comprising, at a tip of the insertion member, a reflecting mirror inclined relative to the optical axis.

7. A scanning examination apparatus comprising:
   a first light source;
   a light scanning unit configured to scan light from the first light source on a specimen;
   an objective lens configured to form an image of the light scanned in the light scanning unit at the specimen;

a light-detecting unit configured to detect return light emitted from the specimen;

a second light source configured to emit visible light;

a deflecting optical element, disposed between the light scanning unit and the objective lens, for making visible light emitted from the second light source enter the objective lens along an optical axis of the objective lens; and a beam-shaping unit configured to form the visible light from the second light source, which is irradiated onto a surface of the specimen via the objective lens using the deflecting optical element, into a pattern that enables the optical axis of the objective lens to be indicated;

wherein the beam-shaping unit is configured to enable selective switching of the pattern of visible light from the second light source.

8. A scanning examination apparatus according to claim 7, wherein the deflecting optical element is formed of a half-mirror.

9. A scanning examination apparatus according to claim 7, wherein the second light source is a wavelength-switchable light source.

10. A scanning examination apparatus according to claim 7, further comprising:

an examination apparatus main body;

a lens unit configured to be removably attached to the examination apparatus main body, the lens unit including the objective lens; and a pointed insertion member formed of an optically transparent material, provided at the end of the lens unit to protrude along the optical axis, wherein the focal position of the lens unit is disposed outside the tip of the insertion member.

11. A scanning examination apparatus according to claim 10 further comprising, at a tip of the insertion member, a transmissive surface orthogonal to the optical axis.

12. A scanning examination apparatus according to claim 10 further comprising, at a tip of the insertion member, a reflecting mirror inclined relative to the optical axis.

13. A scanning examination apparatus comprising:

a first light source;

a light scanning unit configured to scan light from the first light source on a specimen;

an objective lens configured to form an image of the light scanned in the light scanning unit at the specimen;

a light-detecting unit configured to detect return light emitted from the specimen;

a second light source configured to emit visible light;

a deflecting optical element, disposed between the light scanning unit and the objective lens, for making visible light emitted from the second light source enter the objective lens along an optical axis of the objective lens;

a beam-shaping unit configured to form the visible light from the second light source, which is irradiated onto a surface of the specimen via the objective lens using the deflecting optical element, into a pattern that enables the optical axis of the objective lens to be indicated;

an examination apparatus main body;

a lens unit configured to be removably attached to the examination apparatus main body, the lens unit including the objective lens;

a pointed insertion member formed of an optically transparent material, provided at the end of the lens unit to protrude along the optical axis, wherein the focal position of the lens unit is disposed outside the tip of the insertion member; and at a tip of the insertion member, a reflecting mirror inclined relative to the optical axis.

14. A scanning examination apparatus according to claim 13, wherein the deflecting optical element is formed of a half-mirror.

15. A scanning examination apparatus according to claim 13, wherein the second light source is a wavelength-switchable light source.

16. A scanning examination apparatus comprising:

a first light source;

a light scanning unit configured to scan light from the first light source on a specimen;

an objective lens configured to form an image of the light scanned in the light scanning unit at the specimen;

a light-detecting unit configured to detect return light emitted from the specimen;

a second light source configured to emit visible light;

a deflecting optical element, disposed between the light scanning unit and the objective lens, for making visible light emitted from the second light source enter the objective lens along an optical axis of the objective lens;

a beam-shaping unit configured to form the visible light from the second light source, which is irradiated onto a surface of the specimen via the objective lens using the deflecting optical element, into a pattern that enables the optical axis of the objective lens to be indicated;

an examination apparatus main body;

a lens unit including an objective lens; and an objective-lens adaptor attached at the end of the lens unit;

wherein the objective-lens adaptor includes a pointed insertion member formed of an optically transparent material and a mounting portion configured to attach the insertion member to the end of the lens unit in an on-axis manner, and when the objective-lens adaptor is attached to the lens unit, the focal position of the lens unit is disposed outside the insertion member;

a scanning examination apparatus further comprising, at the tip of the insertion member, a reflecting surface that is inclined relative to the optical axis when the objective-lens adaptor is attached to the end of the lens unit.

* * * * *